US011593518B2

(12) United States Patent
Funane et al.

(10) Patent No.: US 11,593,518 B2
(45) Date of Patent: Feb. 28, 2023

(54) MEDICAL IMAGE PROCESSING APPARATUS AND MEDICAL IMAGE PROCESSING METHOD

(71) Applicant: Hitachi, Ltd., Tokyo (JP)

(72) Inventors: Tsukasa Funane, Tokyo (JP); Masashi Kiguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 844 days.

(21) Appl. No.: 16/505,746

(22) Filed: Jul. 9, 2019

(65) Prior Publication Data
US 2020/0034564 A1 Jan. 30, 2020

(30) Foreign Application Priority Data

Jul. 26, 2018 (JP) .............................. JP2018-140182

(51) Int. Cl.
*G06N 7/00* (2006.01)
*G16H 10/00* (2018.01)
*G06F 21/62* (2013.01)
*G06T 7/00* (2017.01)
*G06T 7/194* (2017.01)
*G16H 30/40* (2018.01)
*G06V 10/44* (2022.01)
(Continued)

(52) U.S. Cl.
CPC ........ *G06F 21/6254* (2013.01); *G06T 7/0012* (2013.01); *G06T 7/194* (2017.01); *G06V 10/443* (2022.01); *G16H 30/40* (2018.01); *G06T 7/11* (2017.01); *G06T 19/20* (2013.01); *G06T 2207/10081* (2013.01); *G06T 2210/41* (2013.01); *G16H 10/60* (2018.01)

(58) Field of Classification Search
CPC ............ G06F 21/6254; G06F 21/6245; G06T 7/0012; G06T 7/194; G06T 7/11; G06T 19/20; G06T 2207/10081; G06T 2210/41; G06T 2207/30201; G06T 2219/2021; G06T 5/005; G06V 10/443; G06V 2201/03; G06V 10/754; G06V 20/653; G06V 40/171; G16H 30/40; G16H 10/60
See application file for complete search history.

(56) References Cited

U.S. PATENT DOCUMENTS

2017/0200256 A1 7/2017 Wiemker et al.
2018/0052971 A1* 2/2018 Hanina ................. G16H 10/60
2019/0043611 A1* 2/2019 Saalbach ............. G06F 21/6254

FOREIGN PATENT DOCUMENTS

JP 2017-529110 A 10/2017

* cited by examiner

*Primary Examiner* — Maroun P Kanaan
(74) *Attorney, Agent, or Firm* — Mattingly & Malur, PC

(57) ABSTRACT

Provided is a medical image processing apparatus including: an image acquisition unit that obtains a medical image of a subject; and an image processing unit that generates a second medical image by applying predetermined image processing on the medical image. The image processing unit includes: a surface area extraction unit that extracts a surface area including information that can lead to individuality determination or identification of the subject, from the medical image; a body orientation determination unit that determines body orientation on the basis of the surface area; a surface area deformation unit that deforms the surface area of the medical image; and an object assignment unit that assigns an object indicating the body orientation to the medical image in which the surface area has been deformed and that generates the second medical image.

7 Claims, 12 Drawing Sheets

(51) Int. Cl.
*G06T 19/20* (2011.01)
*G06T 7/11* (2017.01)
*G16H 10/60* (2018.01)

FIG. 4A
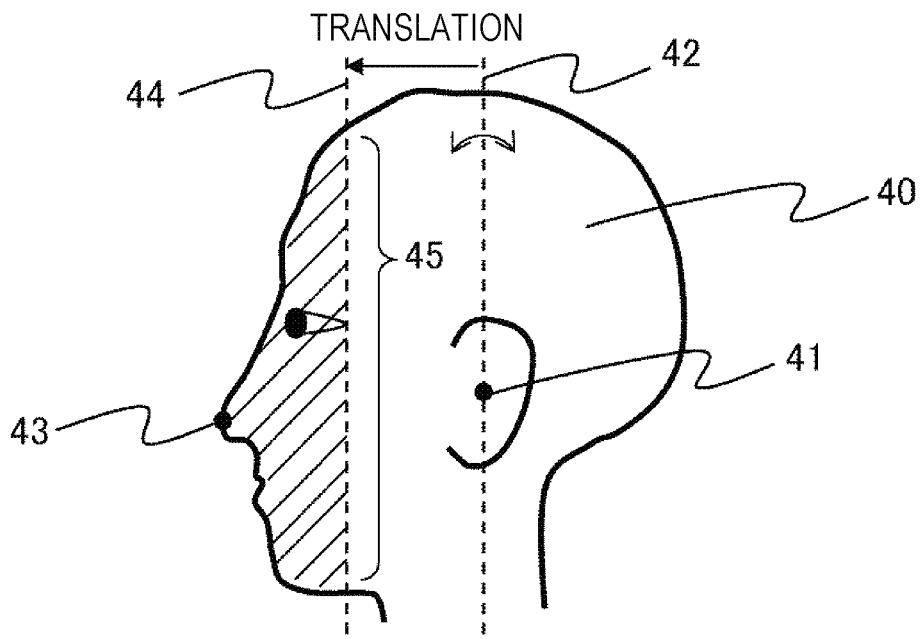
FIG. 4B  FIG. 4C  FIG. 4D
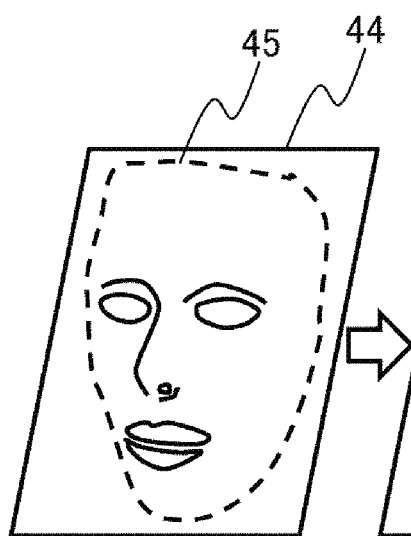 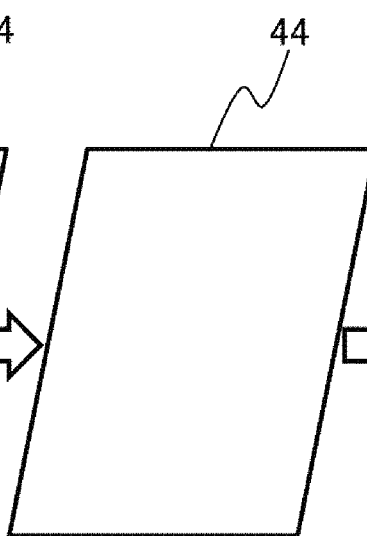 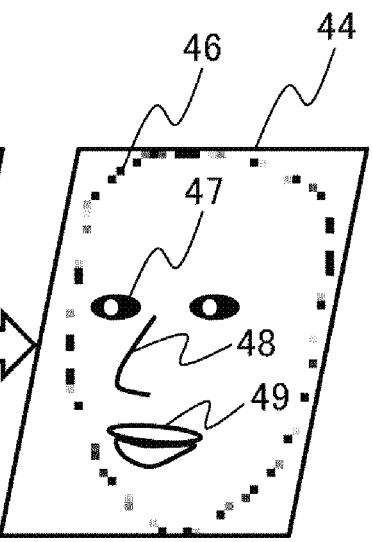

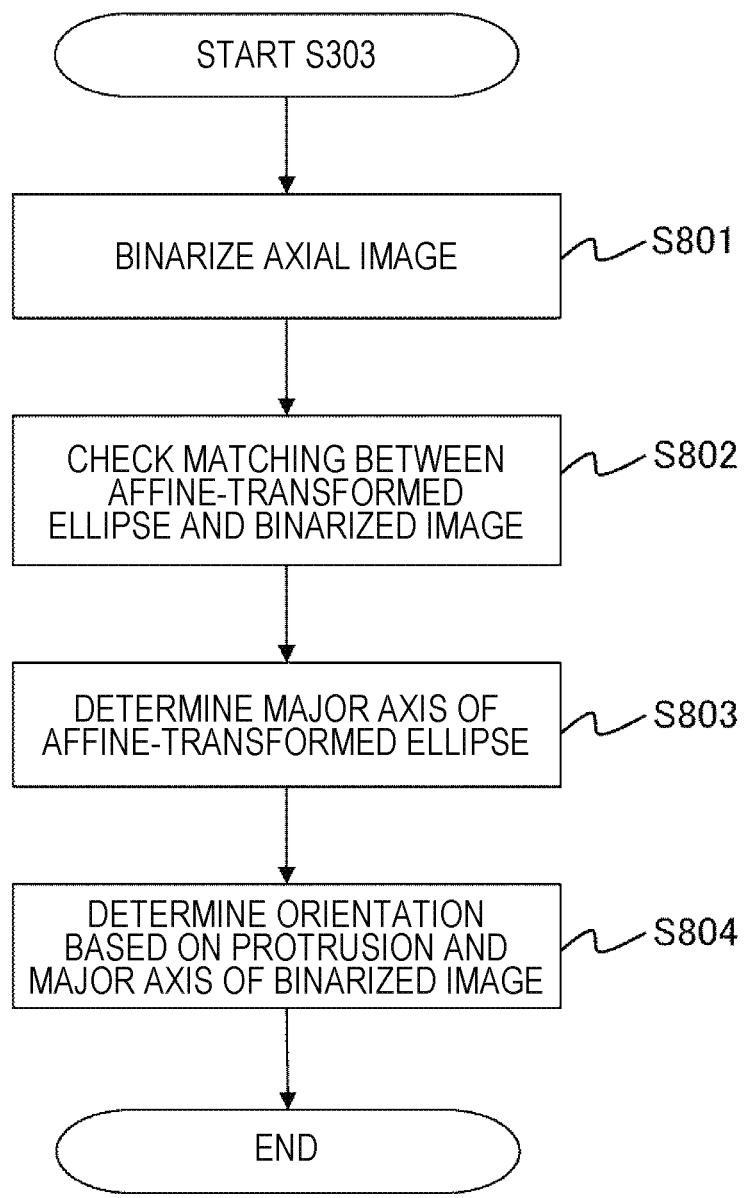

FIG. 11A
FIG. 11B
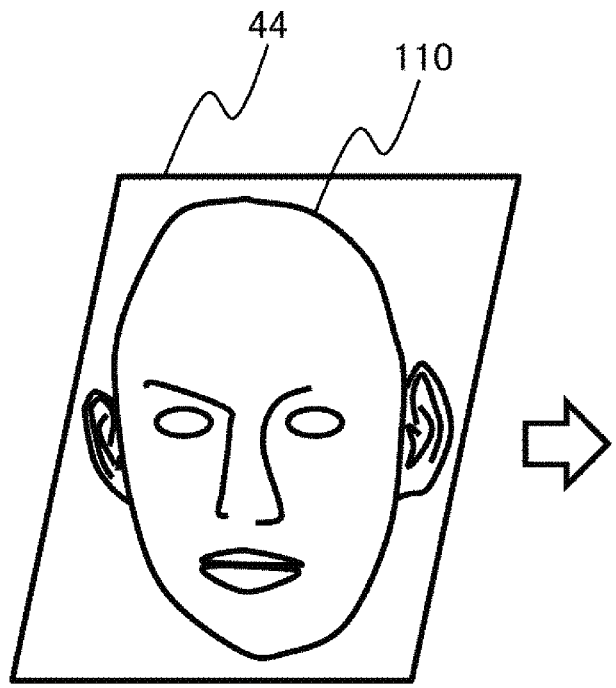
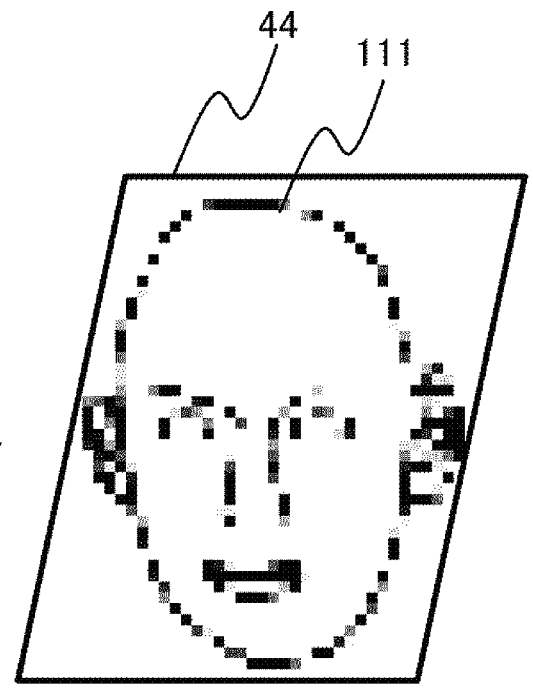

MEDICAL IMAGE PROCESSING APPARATUS AND MEDICAL IMAGE PROCESSING METHOD

CLAIM OF PRIORITY

The present application claims priority from Japanese Patent Application JP 2018-140182 filed on Jul. 26, 2018, the content of which is hereby incorporated by references into this application.

BACKGROUND OF THE INVENTION

1. Field of the Invention

The present invention relates to a medical image processing apparatus, and more particularly to a technology of performing image processing without interfering with diagnosis while deleting information that can lead to individuality determination or identification.

2. Description of the Related Art

Medical images of a subject obtained by magnetic resonance imaging (MRI) device and an X-ray computed tomography (CT) device are used for basic research of diseases in addition for diagnosis of disease of the subject as individual. A surface area of a medical image includes face and appearance being information that can lead to individuality determination or identification, that is, a medical image alone (pixel data) includes information that can lead to individuality determination or identification even when the image does not include the name of the subject, or the like. From the viewpoint of protecting personal information or privacy, information that can lead to individuality determination or identification need to be deleted and anonymized in a case where medical images are used for basic research or the like.

In JP 2017-529110 A discloses image processing that separates three-dimensional image data into a target area and a background area, and then applies randomization processing to the background area to partially randomize the three-dimensional image data, thereby transforming the image data to anonymized image data.

SUMMARY OF THE INVENTION

However, in image data obtained by image processing of JP 2017-529110 A, while the background area including information that can lead to individuality determination or identification is randomized and the information that can lead to individuality determination or identification is deleted from the medical image, this image processing also deletes information related to body orientation in pixel data and thus might interfere with diagnosis.

Accordingly, an object of the present invention is to provide a medical image processing apparatus and a medical image processing method capable of suppressing interference with diagnosis while deleting information that can lead to individuality determination or identification, from a medical image.

In order to achieve the above object, the present invention is a medical image processing apparatus including: an image acquisition unit that obtains a medical image of a subject; and an image processing unit that generates a second medical image by applying predetermined image processing on the medical image, in which the image processing unit includes: a surface area extraction unit that extracts a surface area including information that can lead to individuality determination or identification of the subject, from the medical image; a body orientation determination unit that determines body orientation on the basis of the surface area; a surface area deformation unit that deforms the surface area of the medical image; and an object assignment unit that assigns an object indicating the body orientation to the medical image in which the surface area has been deformed and that generates the second medical image.

Furthermore, the present invention includes a medical image processing method including: obtaining a medical image of a subject; and generating a second medical image by applying predetermined image processing on the medical image, in which the generating includes: extracting a surface area including information that can lead to individuality determination or identification of the subject, from the medical image; determining body orientation on the basis of the surface area; deforming the surface area of the medical image; and assigning an object indicating the body orientation to the medical image in which the surface area has been deformed and that generates the second medical image.

According to the present invention, it is possible to provide a medical image processing apparatus and a medical image processing method capable of suppressing interference with diagnosis while deleting information that can lead to individuality determination or identification from a medical image.

BRIEF DESCRIPTION OF THE DRAWINGS

FIGS. 4A to 4D are views supplementarily illustrating image processing of the first embodiment;

FIG. 8 is a view illustrating an example of a flow of body orientation identification processing of the second embodiment;

FIGS. 11A and 11B are views illustrating an example of the blur processing of the fourth embodiment.

DESCRIPTION OF THE PREFERRED EMBODIMENTS

Figure 1:
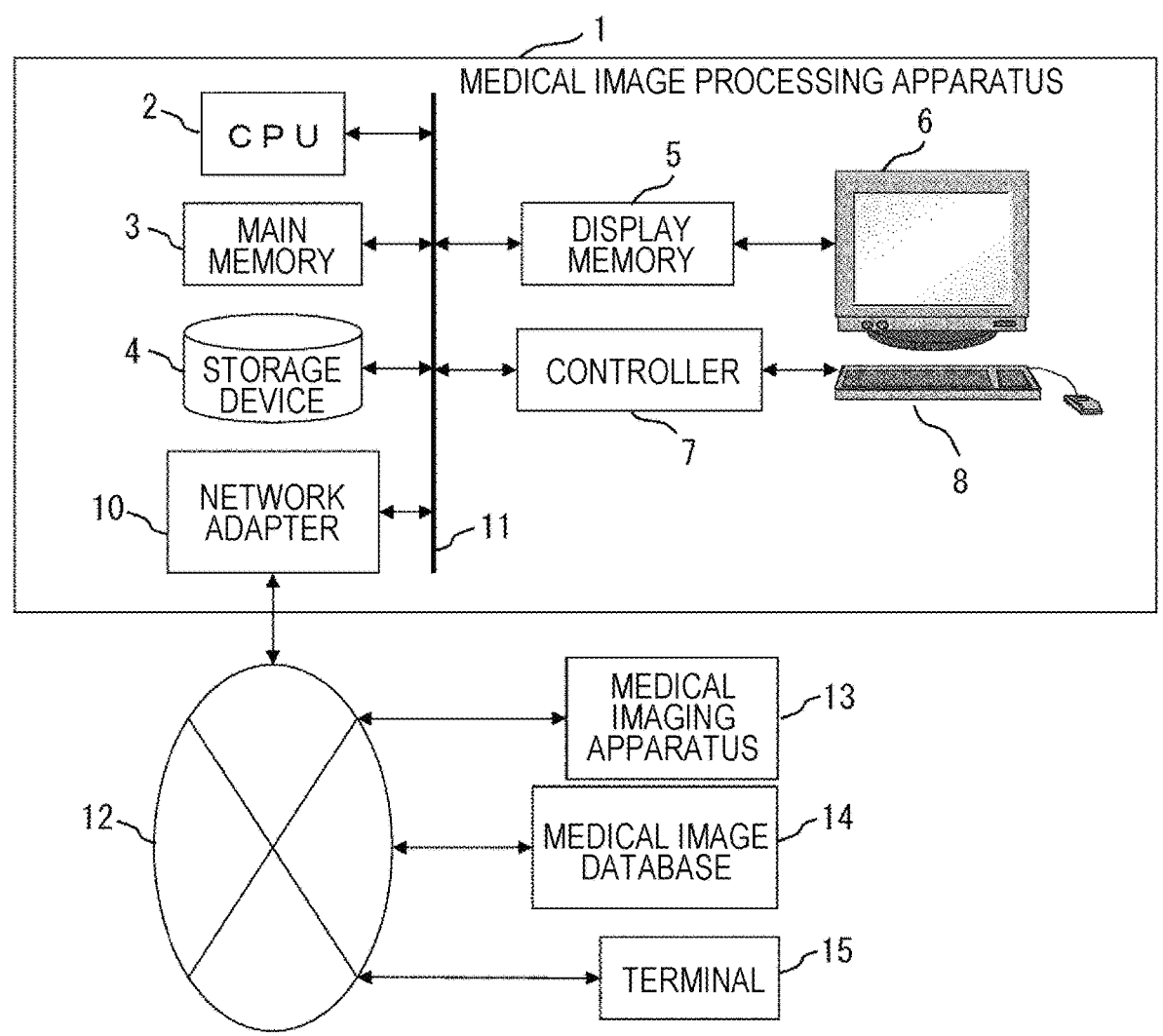
FIG. 1 is an overall configuration diagram of a medical image processing apparatus 1.

Hereinafter, preferred embodiments of a medical image processing apparatus and a medical image processing method according to the present invention will be described with reference to the attached drawings. In the following description and the accompanying drawings, constituents having the same functional configuration will be denoted by same reference numerals and redundant description will be omitted.

First Embodiment

FIG. 1 is a diagram illustrating a hardware configuration of a medical image processing apparatus 1. The medical image processing apparatus 1 has a configuration in which a central processing unit (CPU) 2, a main memory 3, a storage device 4, a display memory 5, a display device 6, a controller 7, an input device 8 and a network adapter 10 are connected to each other via a system bus 11 so as to enable signal transmission and reception. The medical image processing apparatus 1 is connected to a medical imaging apparatus 13 and a medical image database 14 via a network 12 so as to enable signal transmission and reception. Here, "enabling signal transmission and reception" indicates a state in which two-way or one-way optical signal transmission and reception is possible via regardless of wired or wireless communication.

The CPU 2 is a device that controls operation of individual constituents. The CPU 2 loads a program stored in the storage device 4 and data necessary for program execution into the main memory 3 and executes the program. The storage device 4 is a device that stores the program executed by the CPU 2 and data necessary for program execution, represented by a hard disk or the like. Various data are transmitted and received via the network 12 such as a LAN (Local Area Network). The main memory 3 stores a program executed by the CPU 2 and progress of arithmetic processing.

The display memory 5 temporarily stores display data to be displayed on the display device 6 such as a liquid crystal display. The input device 8 is an operation device used by an operator to perform instruction onto the medical image processing apparatus 1, represented by a keyboard, a mouse or the like. The mouse may be substituted by another pointing device such as a track pad or track ball. The controller 7 detects a state of the keyboard or mouse and outputs detected information or the like to the CPU 2. In a case where the display device 6 is a touch panel, the touch panel also functions as the input device 8. The network adapter 10 is used for connecting the medical image processing apparatus 1 to the network 12 such as a local area network (LAN), a telephone line, and the Internet.

The medical imaging apparatus 13 is an apparatus for obtaining a medical image such as a tomographic image of a subject, represented by a magnetic resonance imaging (MRI) apparatus, an X-ray computed tomography (CT) apparatus, an X-ray apparatus, an ultrasound diagnostic apparatus, an ultrasound CT apparatus, a positron emission tomography (PET), or an optical CT device. The medical image database 14 is a database system that stores medical images obtained by the medical imaging apparatus 13. A terminal 15 is used to access the medical image processing apparatus 1 and has a hardware configuration similar to the medical image processing apparatus 1.

Figure 2:
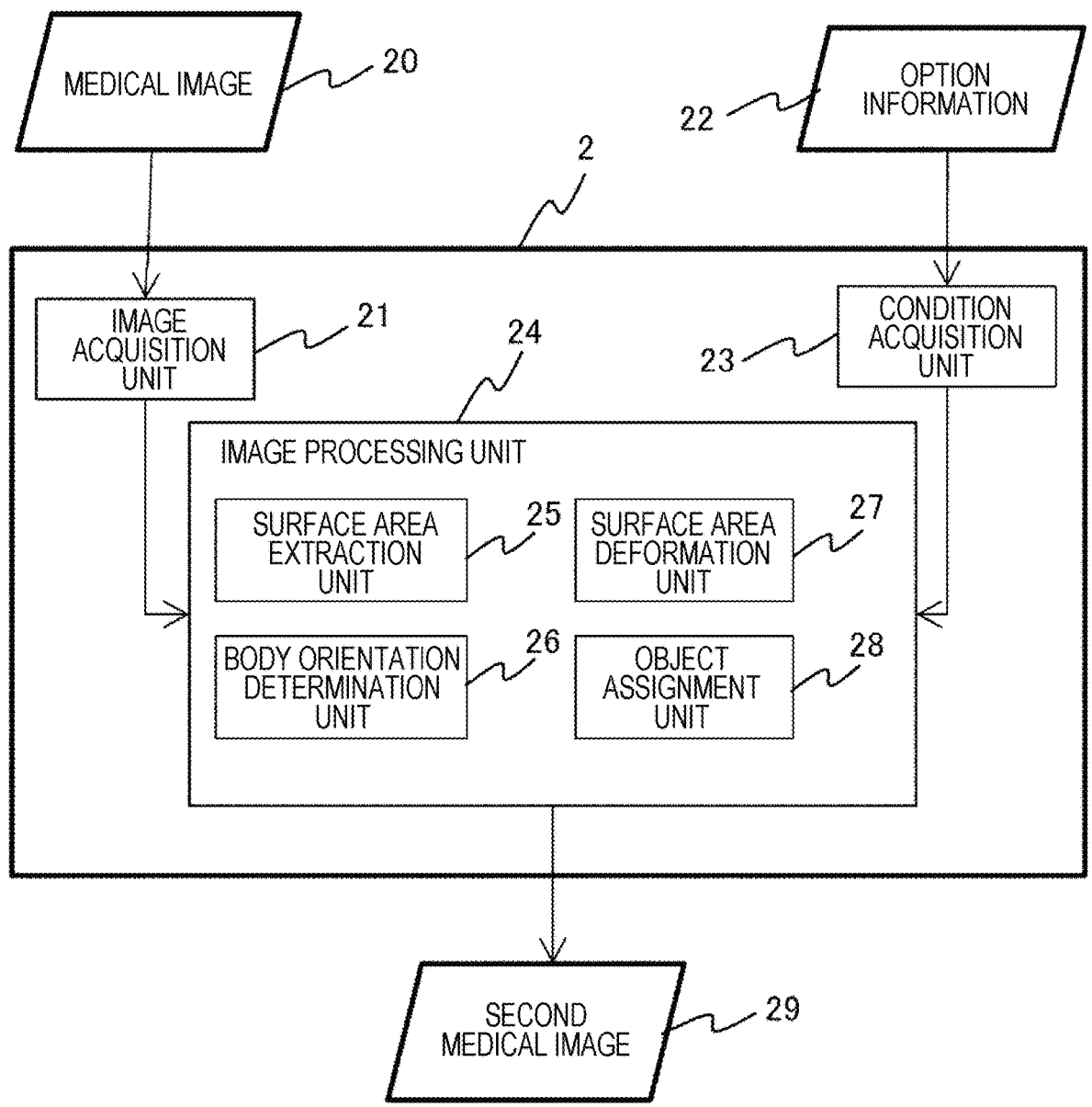
FIG. 2 is a functional block diagram of a first embodiment.

Key components of the present embodiment will be described with reference to FIG. 2. Note that these key components may be configured by dedicated hardware or by software operating on the CPU 2. In the following description, a case where the key components of the present embodiment are configured by software will be described. The present embodiment includes an image acquisition unit 21, a condition acquisition unit 23, and an image processing unit 24. Each of the units will be described below.

The image acquisition unit 21 obtains a medical image 20 as a target of image processing. The medical image 20 may be an image stored in the storage device 4 or may be an image obtained from the medical imaging apparatus 13 or the medical image database 14 via the network adapter 10.

The condition acquisition unit 23 obtains option information 22 used for image processing. The option information 22 is information related to a site to be deleted from the medical image 20. For example, in a case where the medical image 20 is an image of a head, this information corresponds to information related to a site that can lead to individuality determination or identification, such as eyes, nose, mouth, or ears. More specifically, the information would be related to the position, size, or shapes of the eyes, nose, mouth, or ears, aspect ratio of the face, aspect ratio of the ear, and two internal angles out of three in a triangle connecting eyes and protrusion of the nose, or the like. The condition acquisition unit 23 may obtain information on eyes, nose, mouth, and ears designated by an operator by using the input device 8 on the medical image 20.

The image processing unit 24 performs predetermined image processing on the medical image 20 and generates a second medical image 29. The image processing unit 24 according to the present embodiment includes a surface area extraction unit 25, a body orientation determination unit 26, a surface area deformation unit 27, and an object assignment unit 28. Each of the units will be described below.

The surface area extraction unit 25 extracts a surface area including information that can lead to individuality determination or identification of a subject, from the medical image 20. For example, in a case where the medical image 20 is a head image, a surface area including eyes, nose, mouth, and ears is extracted. The surface area may be extracted on the basis of the information obtained by the condition acquisition unit 23, for example, the positions of the eyes, nose, mouth, and ears designated on the medical image 20 by the operator using the input device 8.

The body orientation determination unit 26 determines the body orientation on the basis of the surface area extracted by the surface area extraction unit 25. For example, in a case where the medical image 20 is a head image, the extracted surface area includes the eyes, nose, mouth, and ears. Accordingly, which direction is determined as a front side, namely ventral, and which direction is an upper side, namely, cranial, on the body is determined on the basis of the positions of the eyes, nose, mouth, and ears. For example, the side containing an area including eyes, nose, and mouth is determined as the front side, and a direction in which the mouth, nose, and eyes are arranged in order is determined as an upward direction. Determination of the front and the upper sides leads to determination of the left and right directions of the body.

The surface area deformation unit 27 deforms a surface area of the medical image 20. Specifically, the surface area is deleted from the medical image 20, noise is added to the surface area of the medical image 20, or blur processing is applied on the surface area of the medical image 20. Note that deformation of the surface area of the medical image 20 is performed to make individuality determination or identification substantially impracticable. With this processing, information that can lead to individuality determination or identification is deleted from the medical image 20.

The object assignment unit 28 assigns an object indicating body orientation to the medical image having a deformed surface area and generates the second medical image 29. Examples of the object indicating body orientation include an eye object, a nose object, and a mouth object, simulating the eye, nose, and mouth, respectively, or an arrow or a text indicating body orientation. The eye object, the nose object and the mouth object may be created in sizes different from the sizes of the original eyes, nose and mouth, or assigned at positions shifted from the positions of the original eyes, nose and mouth. However, the deviation from the original position is limited to an extent that would not cause misunderstanding on the operator about the body orientation. That is, the eye object, the nose object, and the mouth object are arranged on the front side of the body, the eye object is arranged on the upper side (forehead side) of the nose object, and the mouth object is arranged on the lower side (jaw side) compared with the nose object.

An example of a flow of processing executed by the medical image processing apparatus 1 including the above-described units will be described with reference to FIG. 3. Each of steps will be described below.

(S301)

The image acquisition unit 21 obtains the medical image 20. The medical image 20 may be obtained from the storage device 4 or may be obtained from the medical imaging apparatus 13 or the medical image database 14. In the present embodiment, a case where a three-dimensional volume image 40 of the head illustrated in FIG. 4A is obtained will be described. FIG. 4A is a side view of the three-dimensional volume image 40 of the head.

In addition, the condition acquisition unit 23 may obtain the option information 22 in the same step. In a case where the operator designates a site via the input device 8, information related to the designated site, for example, a site such as eyes, nose, mouth, or ears is obtained as the option information 22.

(S302)

Figure 5:
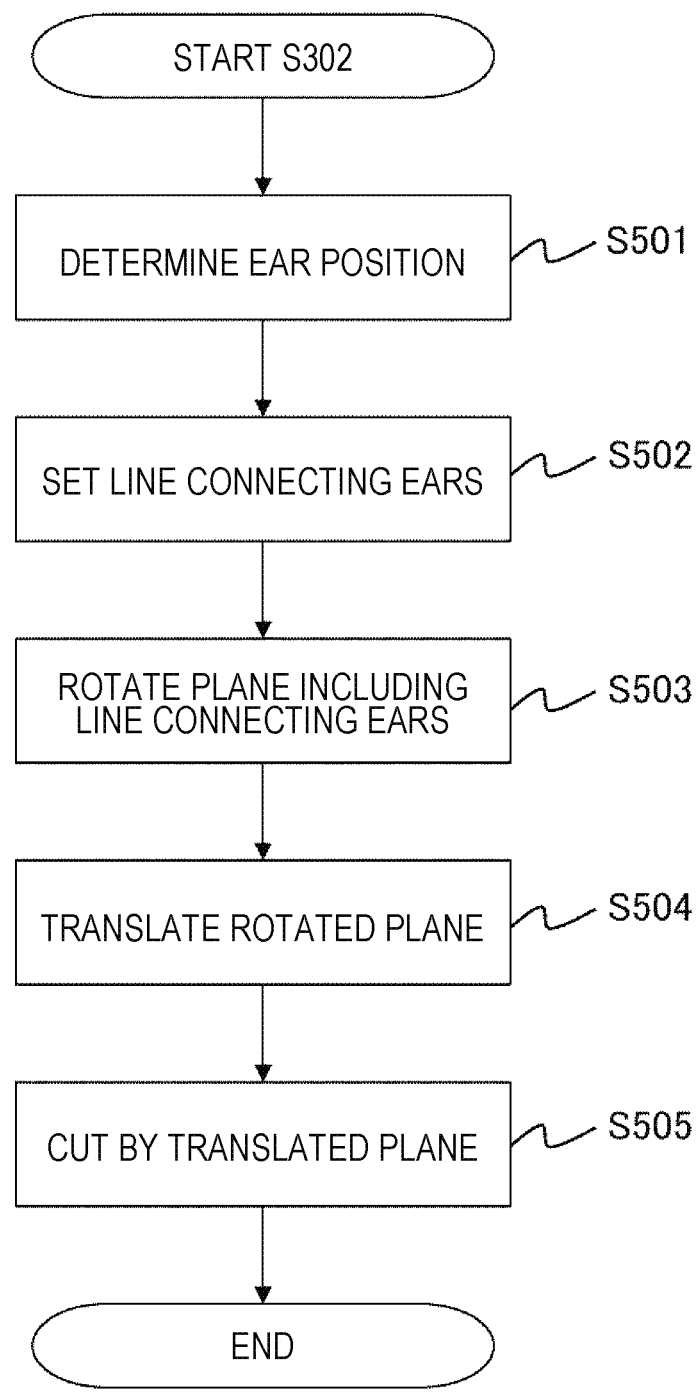
FIG. 5 is a chart illustrating an example of a flow of surface area extraction processing in the first embodiment.

The surface area extraction unit 25 extracts a surface area including information that can lead to individuality determination or identification of the subject from the medical image 20. An example of a flow of processing of extracting the surface area is illustrated in FIG. 5. Hereinafter, each of steps of FIG. 5 will be described with reference to FIGS. 4A to 4D.

(S501)

The surface area extraction unit 25 uses pattern matching or the like and extracts ears from the three-dimensional volume image 40 of the head, and determines the positions of the ears. In a case where the operator designates the positions of the ears, the designated positions of the ears may be used in the subsequent processing.

(S502)

The surface area extraction unit 25 sets a line connecting center points 41 of both ears determined in S501.

(S503)

The surface area extraction unit 25 sets a plane 42 including the line set in S502. The surface area extraction unit 25 further rotates the plane 42 about the line connecting the center points 41 as a rotation axis, and stops rotation of the plane 42 at a position where a distance from the nose projection 43 to the plane 42 is maximized.

(S504)

The surface area extraction unit 25 translates the rotated plane 42 to the nose projection 43 side, and stops the plane 42 when it comes in contact with any of the eye, nose, or mouth.

(S505)

The surface area extraction unit 25 cuts the three-dimensional volume image 40 of the head by the translated plane 44, and then, extracts an area on nose projection 43 side from the plane 44, as a surface area. In FIG. 4A, the surface area is indicated by a hatched area. In the present embodiment, since the plane 44 cuts across the face, the plane 44 is referred to as a face cross section 44, and a boundary 45 of the face cross section 44 and the three-dimensional volume image 40 of the head is referred to as a face boundary 45. FIG. 4B is an example indicating a face area being an example of the extracted surface area on the face cross section 44. Note that the face cross section 44 may be designated on the medical image 20 by the operator using the input device 8.

Figure 6:
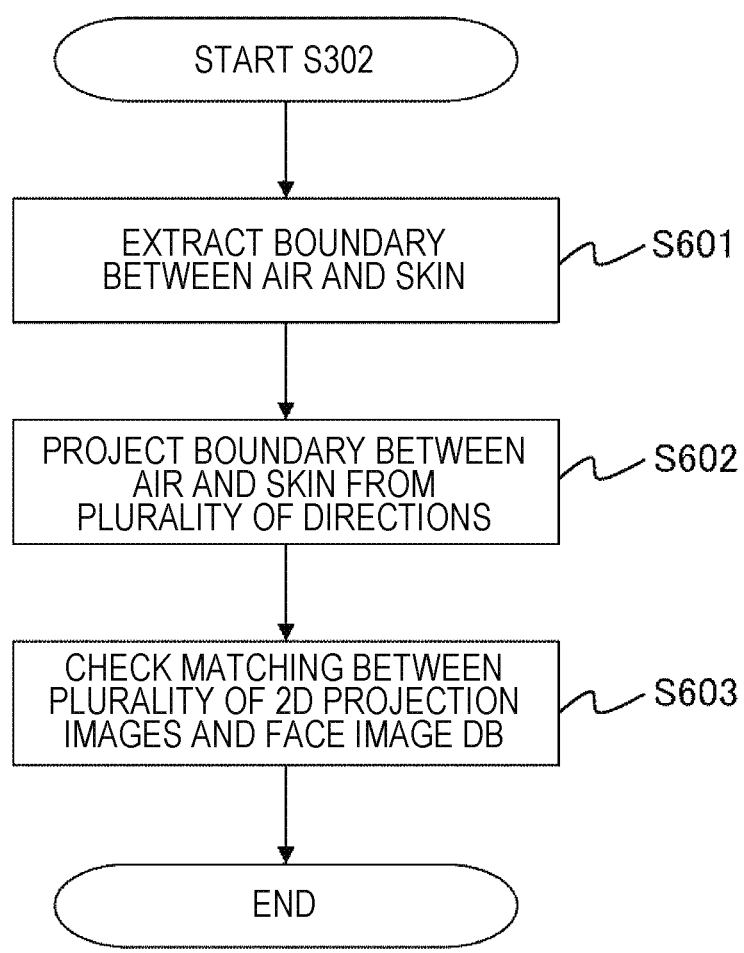
FIG. 6 is a chart illustrating another example of a flow of surface area extraction processing in the first embodiment.

Another example of a flow of the processing of extracting the surface area is illustrated in FIG. 6, and each of steps of FIG. 6 will be described below.

(S601)

The surface area extraction unit 25 executes threshold processing or the like on the three-dimensional volume image 40 of the head and extracts a boundary between air and skin.

(S602)

The surface area extraction unit 25 executes projection processing from a plurality of directions on the boundary between air and skin extracted in S601, and thereby obtains a plurality of two-dimensional projection images, that is, images of the subject surface viewed in two dimensions.

(S603)

The surface area extraction unit 25 checks matching between the plurality of two-dimensional projection images obtained in S602 and a face image database. The face image database is a database in which a plurality of two-dimensional projection images different in shape and size is associated with the surface area. The matching in this step calculates a correlation coefficient between the two-dimensional projection image obtained in S602 and the face image database, and obtains a surface area corresponding to the two-dimensional projection image having the highest correlation coefficient, as a face area. Note that, instead of calculating the correlation coefficient with the face image database, it is allowable to use a classifier such as a neural network or support vector machine that has already learned a front image of a human face so as to define a surface area corresponding to an image with the highest probability of being in a front face direction, as the face area.

Figure 3:
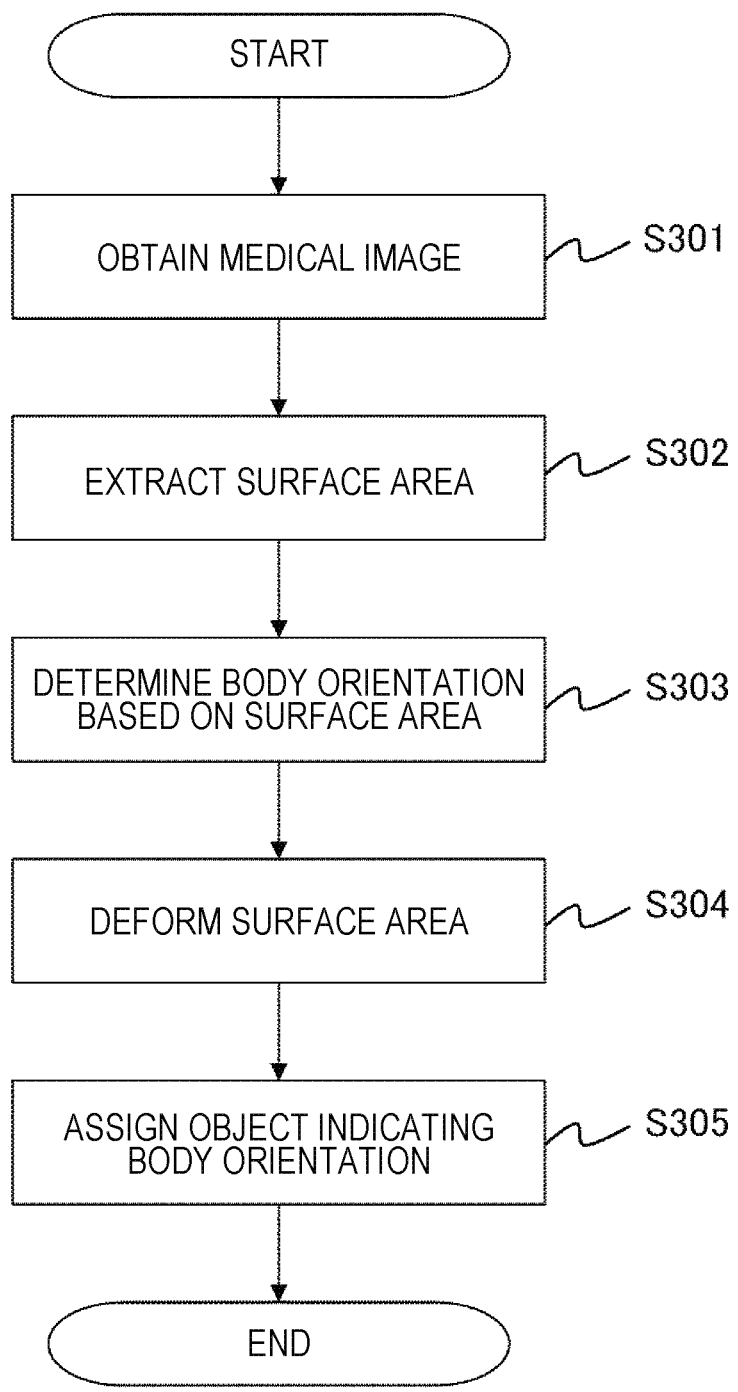
FIG. 3 is a chart illustrating an example of a flow of image processing in the first embodiment.

Now, returning to description of FIG. 3.

(S303)

The body orientation determination unit 26 determines body orientation on the basis of the surface area extracted by the surface area extraction unit 25. Since the surface area in the present embodiment includes eyes, nose and mouth, the body orientation is determined on the basis of the positions of the eyes, nose and mouth. For example, the left side of FIG. 4A is determined as the front side of the body, the upper side of FIG. 4A is as the upper side of the body, and the front side on the sheet of FIG. 4A is as the left side of the body.

(S304)

The surface area deformation unit 27 deforms the surface area of the medical image 20. In the present embodiment, the face area being the surface area is to be deleted, and as a result, an image in FIG. 4B is changed to an image in FIG. 4C. Deletion of the surface area can be performed, for example, by replacing a voxel value of the surface area with 0, or replacing the value with an average value of the voxel values of the surface area, or replacing the value with a random value. The deletion of the face area would make it substantially impracticable to perform individuality determination or identification.

(S305)

The object assignment unit 28 assigns an object indicating body orientation to the medical image having a deformed surface area and generates the second medical image 29. The generated second medical image 29 is displayed on the display device 6 or stored in the storage device 4. After generation of the second medical image 29, the medical image 20 including information that can lead to individuality determination or identification is deleted.

In the present embodiment, as shown in FIG. 4D, an eye object 47, a nose object 48, and a mouth object 49 are assigned to the image of FIG. 4C. Since the eye object 47, nose object 48, and mouth object 49 are created by adding random noise to data of eyes, nose, and mouth with original size and shapes. Accordingly, these objects have modes differing from the original eyes, nose, and mouth, making it possible to keep individuality determination or identification substantially impracticable. The random number seed used for random noise generation and the method of random number generation are changed every time from among a plurality of options. T random number seed that has been used is to be deleted after noise assignment so as to prevent reproduction of the whole random number. The eye object 47, the nose object 48, and the mouth object 49 are arranged at positions shifted from the original positions while maintaining the positional relationship between the eyes, nose and mouth. Therefore, the operator cannot determine or identify the individual even through the operator can grasp the body orientation.

Furthermore, blur processing using a median filter having a diameter of about 3 cm may be applied on the face boundary 45 and thereby generates a blurring boundary 46. Thereafter, the blurring boundary 46 may be added to the second medical image 29 to make it further impracticable to perform individuality determination or identification.

According to the processing flow described above, an object indicating the body orientation is assigned to a medical image while information that can lead to individuality determination or identification is deleted from the medical image. Accordingly, it is possible to suppress interference with diagnosis while making it substantially impracticable to perform individuality determination or identification. Note that, since the medical image 20 is deleted and not stored in the medical image processing apparatus 1, the terminal 15 can access to the second medical image 29 alone, from which individuality determination or identification is substantially impracticable.

Second Embodiment

The first embodiment has described the case where the three-dimensional volume image 40 of the head is obtained. The medical image obtained by the image acquisition unit 21 is not limited to the three-dimensional volume image 40 of the head, and may be another medical image. In the present embodiment, a case where an axial image of a head (an image taken in a body axial section) is obtained will be described. Since the overall configuration of the present embodiment is the same as the first embodiment, description will be omitted.

Figure 7A:
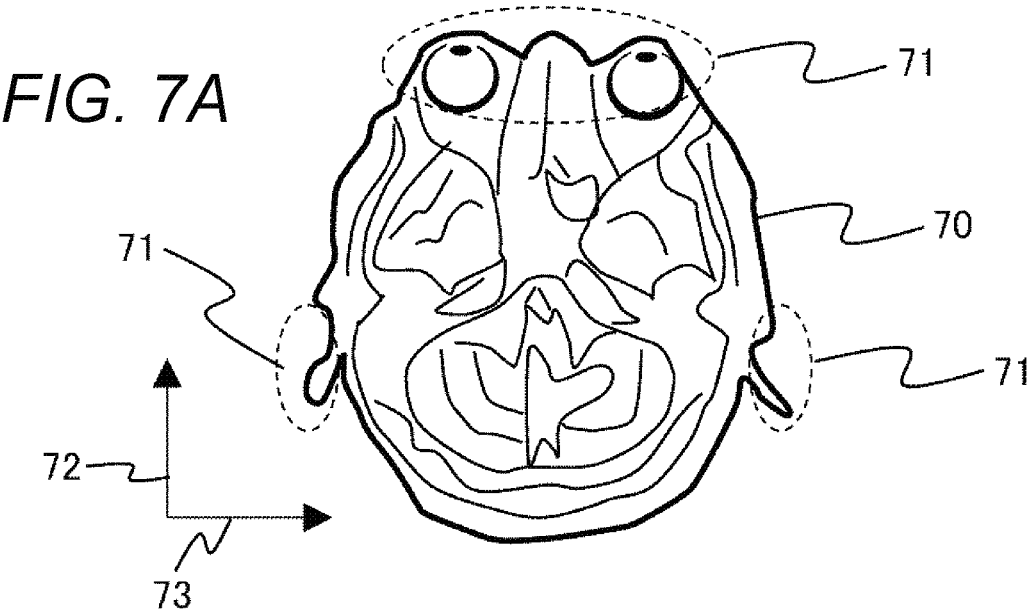
FIGS. 7A and 7B are views illustrating an example of a flow of image processing according to a second embodiment.
Figure 7B:
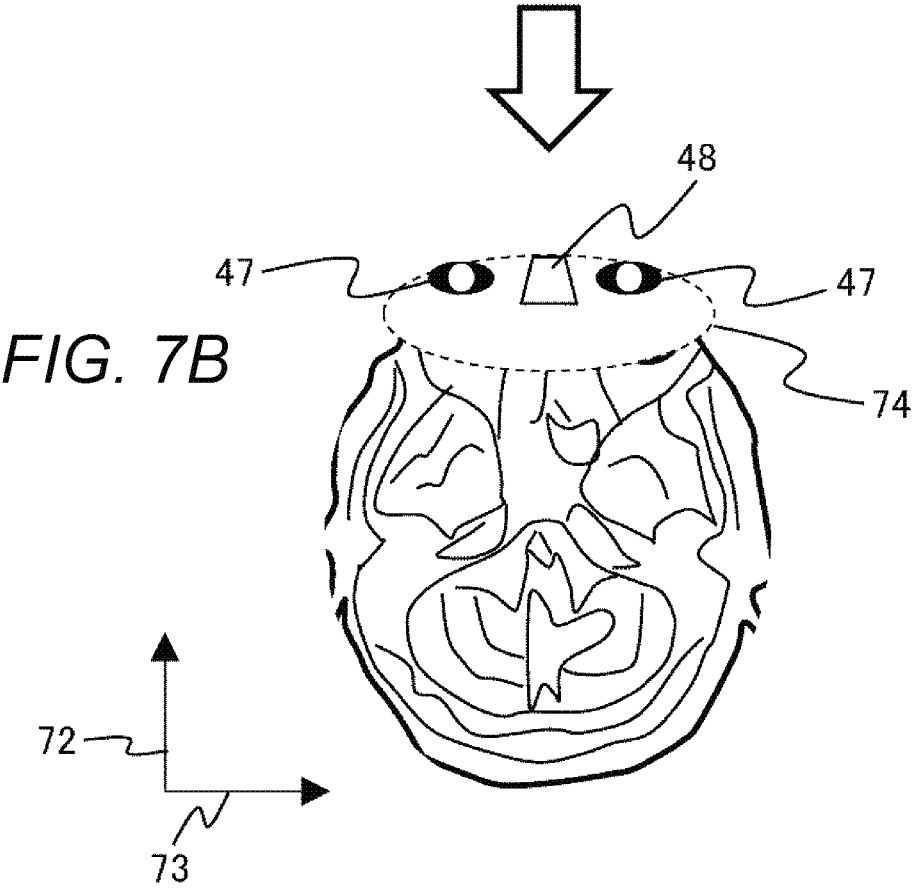

The present embodiment will be described with reference to FIGS. 7A and 7B, along a processing flow of FIG. 3. Description of the processing same as the processing of the first embodiment will be omitted.

(S301)

The image acquisition unit 21 obtains the medical image 20. In the present embodiment, an axial image 70 of the head illustrated in FIG. 7A is obtained as the medical image 20.

(S302)

The surface area extraction unit 25 extracts a surface area including information that can lead to individuality determination or identification of the subject from the medical image 20. In order to extract a surface area, the surface area extraction unit 25 determines a protrusion 71 of the axial image 70 of the head, and uses pattern matching or the like and extracts the nose and ears from the protrusion 71 that has been determined. The surface area extraction unit 25 further extracts an area including the nose and the ears, as the surface area.

Note that the operator may designate the protrusion 71, the nose, and the ears on the axial image 70 of the head.

(S303)

The body orientation determination unit 26 determines body orientation on the basis of the surface area extracted by the surface area extraction unit 25. Since the surface area in the present embodiment includes the eyes, nose and ears, the body orientation is determined on the basis of the positions of the eyes, nose and ears. For example, on the basis of the eye and nose position of the axial image 70 of the head, it is determined that a direction 72 is the front direction of the body. A direction 73 orthogonal to the direction 72 is determined to be any of the left or right direction on the basis of an axial image before and after the axial image 70 of the head. For example, in a case where the axial image before and after the axial image 70 of the head obtained in the front side of the paper surface of FIG. 7B is on the forehead side of the axial image 70, the direction 73 is determined to be the right direction.

Alternatively, the body orientation may be determined by using the fact that the axial image 70 of the head can be approximated by an ellipse. An example of a flow of processing for determining the direction of the head by approximating the axial image 70 of the head with an ellipse is illustrated in FIG. 8, and each of steps in FIG. 8 will be described below.

(S801)

The body orientation determination unit 26 applies binarization processing on the axial image 70 of the head to obtain a binarized image, and determines from the binarized image, a boundary of the head, that is, a boundary between air and skin.

(S802)

The body orientation determination unit 26 generates an ellipse of an arbitrary size, and repeats checking of matching with the boundary of the head specified in S801 while performing affine transformation, that is, scaling and rotation processing on the generated ellipse. Specifically, the body orientation determination unit 26 calculates a correlation coefficient between a plurality of affine-transformed ellipses and the boundary of the head, for example, calculates the Pearson's correlation coefficient or Spearman's correlation coefficient so as to select an affine-transformed ellipse having a maximum correlation coefficient.

Prior to the matching, for example, a portion of the protrusion 71 may be preliminarily deleted by deleting a portion which is out of the ellipse in the process of performing scaling on the boundary of the head identified in S801. Partially deleting the protrusion 71 would make it possible to perform the checking of matching in this step with high accuracy.

(S803)

The body orientation determination unit 26 determines a major axis of the ellipse selected in S802.

(S804)

The body orientation determination unit 26 determines the body orientation on the basis of the major axis of the ellipse determined in S803 and the protrusion 71 in the binarized image obtained in S801. For example, the direction of the major axis is determined as a front-back direction of the body, the side having the protrusion 71 corresponding to the nose is determined as a front direction, and the direction with the protrusion 71 corresponding to the ear is determined as a left-right direction.

Now, returning to description of FIG. 3.

(S304)

The surface area deformation unit 27 deforms the surface area of the medical image 20. In the present embodiment, the protrusion 71 is deleted as the surface area.

(S305)

The object assignment unit 28 assigns an object indicating body orientation to the medical image having a deformed surface area and generates the second medical image 29. FIG. 7B illustrates an example of the second medical image 29 of the present embodiment. In FIG. 7B, the protrusion 71 has been deleted, while the eye object 47 and the nose object 48 are assigned as objects indicating the body orientation in an area 74 from which the protrusion 71 has been deleted, as can be seen in comparison with FIG. 7A.

According to the processing flow described above, an object indicating the body orientation is assigned to a medical image while information that can lead to individuality determination or identification is deleted from the medical image. Accordingly, it is possible to suppress interference with diagnosis while making it substantially impracticable to perform individuality determination or identification. In addition, areas to be deleted in the present embodiment are limited to the protrusion 71, minimizing the influence on the accuracy of diagnosis. Note that extraction of eyes, nose, and ears may use a discriminator on which learning by machine learning algorithms such as a deep neural network has been applied.

Third Embodiment

The first embodiment has been described as the case where the three-dimensional volume image 40 of the head is obtained, and the second embodiment has been described as the case where the axial image 70 of the head is obtained. In the present embodiment, a case where a sagittal image (image taken in a sagittal section) is obtained will be described. Since the overall configuration of the present embodiment is the same as the first embodiment, description will be omitted.

Figure 9B:
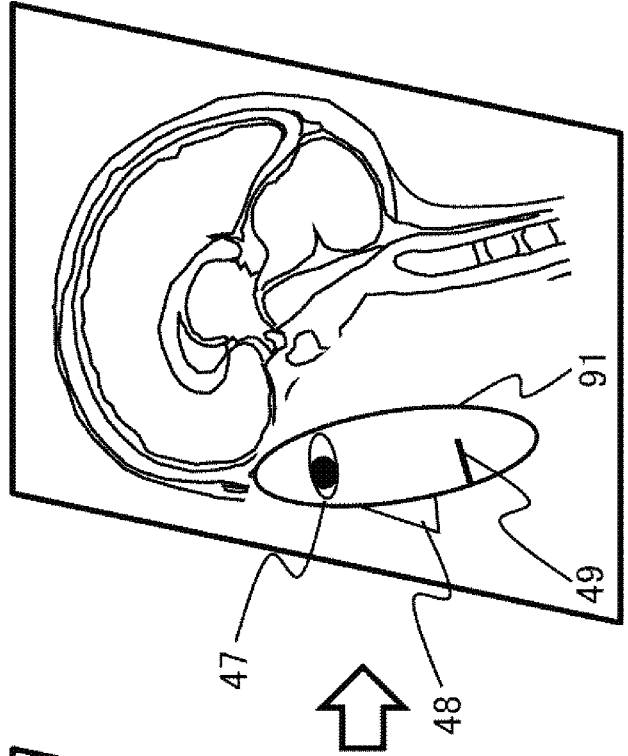
FIGS. 9A and 9B are views illustrating an example of image processing of a third embodiment.
Figure 9A:
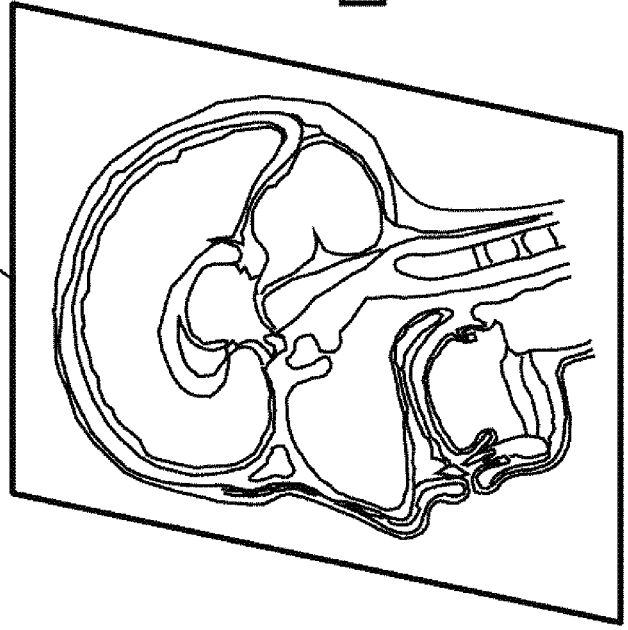

The present embodiment will be described with reference to FIGS. 9A and 9B, along the processing flow of FIG. 3. Description of the processing same as the processing of the first embodiment will be omitted.

(S301)

The image acquisition unit 21 obtains the medical image 20. In the present embodiment, a sagittal image 90 of the head illustrated in FIG. 9A is obtained as the medical image 20.

(S302)

The surface area extraction unit 25 extracts a surface area including information that can lead to individuality determination or identification of the subject from the medical image 20. In order to extract the surface area, the surface area extraction unit 25 uses pattern matching or the like and extracts eyes, a nose, and a mouth from a sagittal image 90 of the head. The surface area extraction unit 25 further extracts an area including eyes, nose, and mouth, as the surface area. The eyes, nose and mouth may be designated by the operator on the sagittal image 90 of the head.

(S303)

The body orientation determination unit 26 determines body orientation on the basis of the surface area extracted by the surface area extraction unit 25. Since the surface area in the present embodiment includes eyes, nose and mouth, the body orientation is determined on the basis of the positions of the eyes, nose and mouth. For example, on the basis of the positions of the eyes, nose, and mouth of the sagittal image 90 of the head, the left side of FIG. 9A is determined as the front direction of the body. Moreover, on the basis of the arrangement of the eyes, nose and mouth, the upper side of FIG. 9A is determined as the upper direction of the body.

(S304)

The surface area deformation unit 27 deforms the surface area of the medical image 20. In the present embodiment, the area including the eyes, nose and mouth is deleted as the surface area.

(S305)

The object assignment unit 28 assigns an object indicating body orientation to the medical image having a deformed surface area and generates the second medical image 29. FIG. 9B illustrates an example of the second medical image 29 of the present embodiment. In FIG. 9B, the area including eyes, nose, and mouth has been deleted, while the eye object 47, the nose object 48, and the mouth object 49 are assigned as objects indicating the body orientation in the area 91 from which the area including the eye, nose, and mouth has been deleted, as can be seen in comparison with FIG. 9A.

According to the processing flow described above, an object indicating the body orientation is assigned to a medical image while information that can lead to individuality determination or identification is deleted from the medical image. Accordingly, it is possible to suppress interference with diagnosis while making it substantially impracticable to perform individuality determination or identification.

Fourth Embodiment

The first embodiment is an example of deleting the surface area as deformation of the surface area in S304 of FIG. 3. The deformation of the surface area is not limited to the deletion of the surface area, and blur processing may be applied on the surface area. In the present embodiment, a case of applying blur processing on the surface area will be described. Since the overall configuration of the present embodiment is the same as the first embodiment, description will be omitted.

Figure 10:
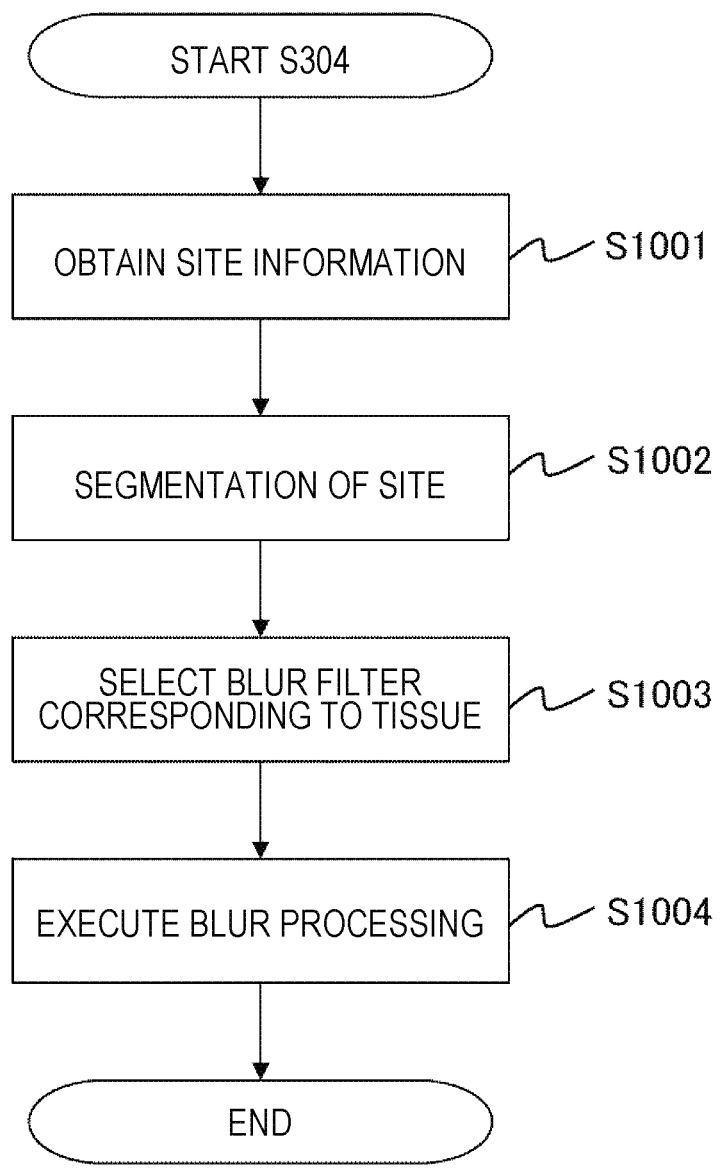
FIG. 10 is a chart illustrating an example of a flow of blur processing being surface area deformation processing according to a fourth embodiment.

The blur processing of the present embodiment will be described along FIG. 10 with reference to FIGS. 11A and 11B. The blur processing of the present embodiment is executed as deformation of the surface area performed in S304 of FIG. 3.

(S1001)

The condition acquisition unit 23 obtains the name of the site on which blur processing is to be applied as site information. The name of the site may be designated by an operator from the input device 8 or may be extracted by the image acquisition unit 21 from supplementary information of the medical image 20. In the present embodiment, a face area 110 on the face cross section 44 illustrated in FIG. 11A is a target of blur processing, and thus, "head" is obtained as the name of the site.

(S1002)

The surface area deformation unit 27 performs segmentation on the medical image 20 on the basis of the site information obtained in S1001. In a case where the site is the head, the medical image 20 is divided into five tissue layers, such as soft tissue such as skin, skull, cerebrospinal fluid, gray matter and white matter. In a case where the site is the upper arm or forearm, the medical image 20 is divided into tissues such as skin layer, fat layer, muscle layer and bone. In the present embodiment, the site information obtained in S1001 is the "head", and thus, the medical image 20 is divided into the above-described five tissue layers.

(S1003)

The surface area deformation unit 27 selects a blur filter in accordance with the tissue divided in S1002. In a case where the site is the head, a blur filter is selected for the soft tissue such as skin or an outer boundary of the skull, involved in individuality determination or identification.

(S1004)

The surface area deformation unit 27 executes blur processing using the blur filter selected in S1003. In application of the blur filter, convolution processing of a predetermined three-dimensional image is performed on the three-dimensional volume image. Alternatively, a three-dimensional moving average filtering, a median filter, a weighted average filter, a Gaussian filter or the like may be used. Note that blur processing may include morphing processing, which is one of methods for smoothly deforming an image. FIG. 11B is an example of a face area 111 after the blur processing on the outer boundary of the skin. The blur processing blurs contour of the face area 110, making it substantially impracticable to perform individuality determination or identification.

The eyes, nose, and mouth blurred by the blur processing still function as objects indicating the body orientation, and thus, S305 of FIG. 3 may either be skipped in the present embodiment, or S305 may be executed to assign the eye object 47 or the like on the blurred face area 111 of FIGS. 11A and 11B.

According to the flow of the processing described above, the body orientation is indicated while making it substantially impracticable to individuality determination or identification. Accordingly, it is possible to suppress interference with diagnosis while making it substantially impracticable to perform determination or identification of individual. Furthermore, according to the present embodiment, the surface area is merely blurred without being deleted, making it possible to maintain visibility of the second medical image 29.

Fifth Embodiment

The first embodiment is an example of deformation of the surface area to delete information that can lead to individuality determination or identification. However, deformation of the surface area might not be desirable depending on the type of disease. In the present embodiment, selection of a deformation target according to the type of disease will be described. Since the overall configuration of the present embodiment is the same as the first embodiment, description will be omitted.

Figure 12:
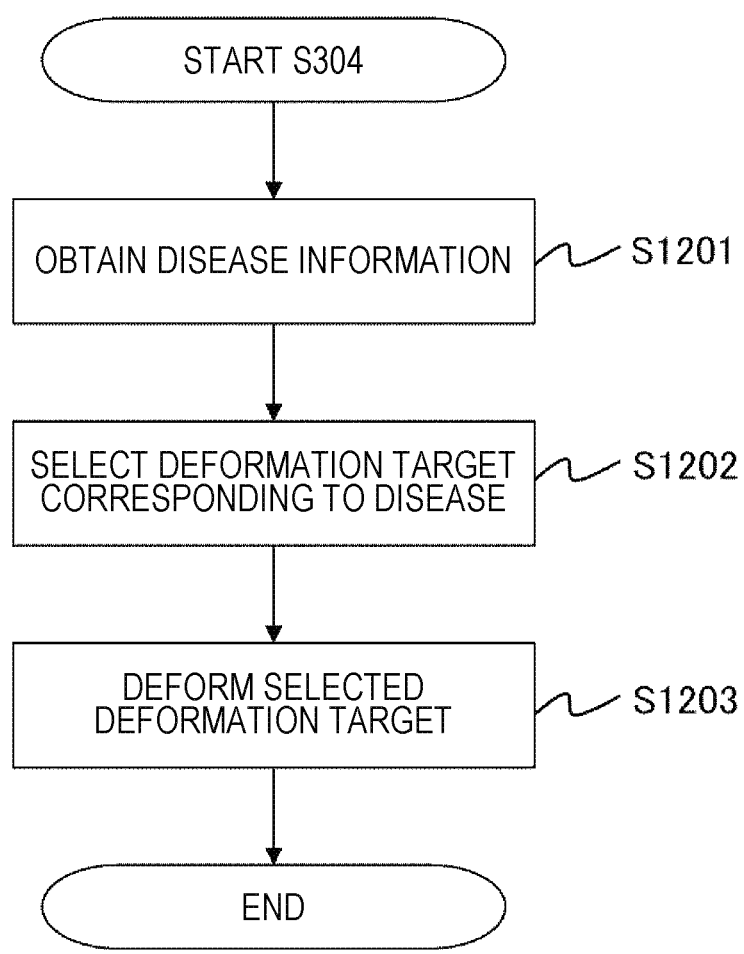
FIG. 12 is a chart illustrating an example of a flow of surface area deformation processing in a fifth embodiment.

The present embodiment will be described with reference to FIG. 12. The processing of the present embodiment is executed in S304 of FIG. 3.

(S1201)

The condition acquisition unit 23 obtains the name of the disease as disease information. The name of the disease may be input from the input device 8 by the operator, may be obtained from the supplementary information of the medical image 20 by the image acquisition unit 21, or may be obtained from an electronic medical record associated with the medical image 20, via the network 12.

(S1202)

The surface area deformation unit 27 selects a deformation target on the basis of the disease information obtained in S1201. A correspondence table associating disease information with a deformation target is used in selection of the deformation target. The correspondence table associates a site other than the brain with the brain disease, and a site other than the eye is associated with the eye in case of eye disease, for example. The correspondence table is created in accordance with a purpose of use. For example, a correspondence table for simple screening or a correspondence table for close examination is created in advance and stored in the storage device 4. The surface area deformation unit 27 reads out the correspondence table from the storage device 4 in accordance with a purpose of use, and selects a deformation target on the basis of the disease information and the correspondence table.

(S1203)

The surface area deformation unit 27 deforms the deformation target selected in S1202. The deformation of the deformation target may be deletion of the deformation target or execution of blur processing on the deformation target.

The above-described flow of processing can appropriately select the deformation target in accordance with the disease, making it possible to make individuality determination or identification substantially impracticable while suppressing interference with diagnosis.

A plurality of embodiments of the present invention has been described as above. The present invention is not limited to the above embodiments, and the constituents may be modified without departing from the scope of the invention. For example, although the medical image of the head is described as an example in many embodiments, medical images other than the head may be used. Furthermore, a plurality of constituents disclosed in the above embodiments may be appropriately combined. Furthermore, some constituents may be deleted from all the constituents illustrated in the above embodiment.

What is claimed is:

1. A medical image processing apparatus comprising:
a processor; and
a memory coupled to the processor, the memory storing instructions that when executed by the processor, configure the processor to:
obtain a medical image of a subject, the medical image being an axial image of an axial section along an axis of a body of the subject,
extract a surface area including potentially identifying information, from the medical image,
apply a binarization process to the axial image to obtain a binarized image,
determine from the binarized image, a boundary of the body of subject in the image,
generate an ellipse of an arbitrary size,
perform a plurality of affine transformations including scaling and rotation processing on the generated ellipse,
calculate a correlation coefficient between a plurality of affine-transformed ellipses and the boundary and select an affine-transformed ellipse having a maximum correlation coefficient,
determine a major axis of the selected ellipse, determine a body orientation based on the major axis of the selected ellipse, deform the surface area of the medical image based on the body orientation, and assign an object indicating the body orientation to the medical image in which the surface area has been deformed and that generates a second medical image including the assigned object indicating the body orientation.

2. The medical image processing apparatus according to claim 1, wherein the processor is configured to deform of the surface area based on blur processing or morphing processing.

3. The medical image processing apparatus according to claim 1, wherein, in a case where the medical image is a head image, the surface area includes any of eyes, nose, mouth, or ears.

4. The medical image processing apparatus according to claim 3, wherein the processor is configured to replace any of the eyes, nose, mouth, or ears included in the surface area, with objects simulating the eyes, nose, mouth, or ears.

5. The medical image processing apparatus according to claim 3, wherein the processor is configured to:

receive a designation of eyes, nose, mouth, and ears related to the potentially identifying information; and obtain information related to the eyes, nose, mouth, and ears, designated on the medical image, extract the surface area on the basis of the obtained information.

6. The medical image processing apparatus according to claim 1, wherein the processor is configured to select a deformation target in accordance with a disease.

7. A medical image processing method comprising:

obtaining a medical image of a subject, the medical image being an axial image of an axial section along an axis of a body of the subject;

extracting a surface area including potentially identifying information of the subject, from the medical image;

applying a binarization process to the axial image to obtain a binarized image;

determining from the binarized image, a boundary of the body of subject in the image;

generating an ellipse of an arbitrary size;

performing a plurality of affine transformations including scaling and rotation processing on the generated ellipse;

calculating a correlation coefficient between a plurality of affine-transformed ellipses and the boundary and select an affine-transformed ellipse having a maximum correlation coefficient;

determining a major axis of the selected ellipse;

determining a body orientation based on the major axis of the selected ellipse;

deforming the surface area of the medical image based on the body orientation; and assigning an object indicating the body orientation to the medical image in which the surface area has been deformed and that generates a second medical image including the assigned object indicating the body orientation.

* * * * *